United States Patent [19]

Foley

[11] Patent Number: 4,544,507

[45] Date of Patent: Oct. 1, 1985

[54] PRODUCTION OF CARBONATE DIESTERS FROM OXALATE DIESTERS

[75] Inventor: Paul Foley, Hazlet, N.J.

[73] Assignee: Celanese Corporation, New York, N.Y.

[21] Appl. No.: 577,101

[22] Filed: Feb. 6, 1984

[51] Int. Cl.[4] .............................................. C07C 68/00
[52] U.S. Cl. ..................................... 260/463; 560/190
[58] Field of Search ......................... 260/463; 560/190

[56] References Cited

U.S. PATENT DOCUMENTS 3,922,275 11/1975 Noda et al. ........................ 544/279
3,994,960 11/1976 Yamakazi et al. .................. 260/463

OTHER PUBLICATIONS

Uchiumi and Yamashita, *J. Japan Petrol. Inst.*, vol. 25, No. 4, (1982), pp. 197–203.
Romano et al., Ind. Eng. Chem. Prod. Res. Dev. 19, pp. 396–403, (1974).

*Primary Examiner*—Donald G. Daus
*Assistant Examiner*—Stephen Kapner
*Attorney, Agent, or Firm*—Depaoli & O'Brien

[57] ABSTRACT

This invention provides a process for the production of a carbonate diester which involves heating an oxalate diester in a liquid medium containing an alcoholate catalyst to yield carbonate diester and carbon monoxide.

12 Claims, No Drawings

PRODUCTION OF CARBONATE DIESTERS FROM OXALATE DIESTERS

DESCRIPTION OF THE INVENTION

Carbonate diesters generally are prepared by the reaction of an alcohol with carbon monoxide.

U.S. Pat. No. 3,227,740 describes a process for preparing a carbonate diester by the reaction of an alkanol and carbon monoxide in the presence of a solution of mercuric salts in an organic solvent:

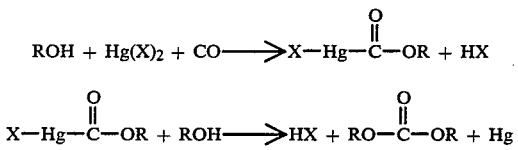

The described process is not suitable for the preparation of aromatic carbonates, and additionally has the disadvantage that mercuric salts are reactive with alcohols at elevated temperatures.

U.S. Pat. No. 3,994,960 describes a process for preparing dialkyl oxalate, with dialkyl carbonate as a byproduct, by the reaction of an alkanol with carbon monoxide and oxygen in the presence of a platinum group metal and copper or iron containing catalyst and an accelerator such as pyridine or sodium carbonate.

J. Japan Petrol. Inst., 25(4), 197 (1982) describes a process for preparing dialkyl oxalate, with dialkyl carbonate as a byproduct, by the reaction of an alkanol with carbon monoxide in the presence of a palladium catalyst and alkyl nitrite.

Ind. Eng. Chem. Prod. Res. Div., 19, 396 (1980) describes a process for the synthesis of dimethyl carbonate which involves the reaction of methanol, carbon monoxide and oxygen in the presence of a copper salt catalyst as a one-step redox system.

There is a need for new and improved methods for synthesizing carbonate diesters in high yield and without difficult product recovery.

Accordingly, it is an object of this invention to provide a novel process for the production of carbonate diesters which does not involve the condensation of alcohol with carbon monoxide.

It is another object of this invention to provide a process for the conversion of oxalate diesters into carbonate diesters.

Other objects and advantages of the present invention shall become apparent from the accompanying description and examples.

DESCRIPTION OF THE INVENTION

One or more objects of the present invention are accomplished by the provision of a process for the production of a carbonate diester which comprises heating an oxalate diester at a temperature between about 50°–150° C. in a liquid medium containing an alcoholate catalyst to yield carbonate diester and carbon monoxide.

The term "alcoholate" refers to a ZO$^-$ structure, which is an anionic radical derived from an alcohol. The counter cation species can be an alkali metal, a quaternary ammonium group, an alkali metal crown ether complex, and the like.

In a further embodiment, this invention provides a process for the production of a carbonate diester which comprises heating an oxalate diester, $RO_2C-CO_2R$, at a temperature between about 50°–150° C. as a liquid phase containing an alkali metal alcoholate catalyst, $R^1-OM$, under anhydrous conditions to yield carbon monoxide and a carbonate diester, $RO-CO-OR$; where R is a substituent selected from aliphatic, alicyclic and aromatic groups containing between about 1–20 carbon atoms, $R^1$ is a hydrocarbon substituent containing between about 1–20 carbon atoms, and M is sodium, potassium or lithium metal.

Illustrative of the R substituents, which may be the same or different groups, in the $RO_2C-CO_2R$ oxalate diester are methyl, ethyl, butyl, allyl, methallyl, pentyl, cyclohexyl, furfuryl, phenyl, chlorophenyl, naphthyl, pyridyl, and the like.

Illustrative of the $R^1$ substituent in the alcoholate catalyst are methyl, ethyl, propyl, butyl, isobutyl, pentyl, hexyl, hexenyl, cyclopentyl, cyclohexyl, phenyl, tolyl, naphthyl, and the like.

The preferred alcoholate catalysts are alkali metal alkoxides containing between about 1–6 carbon atoms, such as sodium methoxide, potassium ethoxide, lithium butoxide, and the like.

The alcoholate component is employed in a quantity sufficient to catalyze the desired conversion of oxalate diester to carbonate diester, e.g., a quantity between about 0.1–5 weight percent of alcoholate dissolved or suspended in the liquid reaction medium, calculated on the weight of oxalate diester.

The process is conducted by heating the oxalate diester at a temperature between about 50°–150° C., preferably 80°–120° C., in contact with an alcoholate catalyst in a liquid phase reaction medium.

The alcoholate catalyst can be dissolved in the liquid medium, or it can be in the form of a solid particulate suspension. When the alcoholate is a particulate suspension in the liquid medium, there must be a sufficient equilibrium quantity of alcoholate dissolved in the liquid medium to effect the desired catalysis.

The liquid medium can comprise the oxalate diester starting material and subsequently the carbonate diester product. Alternatively, an organic solvent can be included as a component of the reaction medium, preferably an inert liquid such as an aprotic solvent. Illustrative of aprotic solvents are diethyl ether, ethylene glycol dimethyl ether, ethyl acetate, glycol diacetate, pentane, hexane, benzene, xylene, dimethyl sulfoxide, carbon disulfide, dimethylformamide, tetrahydrofuran, and the like. The preferred solvents are those which do not contain a hydrogen atom that is reactive with the alcoholate catalyst.

The reaction medium can tolerate the presence of a slight amount of moisture, at the expense of an equivalent loss of alcoholate catalyst. The reaction medium preferably is maintained under anhydrous conditions during the course of the oxalate diester conversion to carbonate diester.

The reaction period will vary between about 0.1–5 hours, and usually will be in the range between about 0.5–3 hours, depending on other process conditions such as temperature, oxalate diester reactivity, alcoholate catalyst activity, and the like.

The carbonate diester product can be recovered by conventional procedures such as fractional distillation.

The following Examples are further illustrative of the present invention. The catalysts and other specific ingredients and processing parameters are presented as being typical, and various modifications can be derived in view of the foregoing disclosure within the scope of the invention.

EXAMPLES

A moisture-free carbon monoxide-flushed autoclave is charged with 50 grams (0.424 mole) of dimethyl oxalate and 5 grams (0.092 mole) of anhydrous sodium methoxide. The reaction medium is heated at a temperature of 100° C. for 1.25 hours, and then cooled to room temperature.

All of the dimethyl oxalate is converted to products, which include dimethyl carbonate (0.251 mole), carbon monoxide (0.315 mole), methyl formate (6 mmoles), methanol (3 mmoles) and dimethyl ether (32 mmoles). Approximately 0.161 mole of the initial dimethyl oxalate charge is not accounted for in the material balance of the recovered products.

All of the product structures are verified by GC/MS analysis.

The procedure is repeated with diethyl oxalate as the reactant, and sodium ethoxide as the catalyst. The main product is diethyl carbonate.

The procedure is repeated with diphenyl oxalate as the reactant, and potassium phenoxide as the catalyst, in a tetrahydrofuran solvent medium under anhydrous conditions. The main product is diphenyl oxalate.

Similar results are obtained when the catalyst is tetramethylammonium methoxide or a complex of 18-crown-6 ether with sodium ethoxide. A detailed description of crown ethers is elaborated in J.A.C.S., 89(10), 2495(1967) and J.A.C.S. 89(29), 7017(1967).

What is claimed is:

1. A process for the production of a carbonate diester which consists of heating an oxalate diester at a temperature between about 50°–150° C. in a liquid medium containing an alcoholate catalyst to yield carbonate diester and carbon monoxide.

2. A process for the production of a carbonate diester which consists of heating an oxalate diester, $RO_2C-CO_2R$, at a temperature between about 50°–150° C. as a liquid phase containing an alkali metal alcoholate catalyst, $R^1-OM$, under anhydrous conditions to yield carbon monoxide and a carbonate diester, $RO-CO-OR$; where R is a substituent selected from aliphatic, alicyclic and aromatic groups containing between about 1–20 carbon atoms, $R^1$ is a hydrocarbon substituent containing between about 1–20 carbon atoms, and M is sodium, potassium or lithium metal.

3. A process in accordance with claim 2 wherein the oxalate diester is dimethyl oxalate, and the carbonate diester product is dimethyl carbonate.

4. A process in accordance with claim 2 wherein the oxalate diester is diethyl oxalate, and the carbonate diester product is diethyl carbonate.

5. A process in accordance with claim 2 wherein the oxalate diester is diphenyl oxalate, and the carbonate diester product is diphenyl carbonate.

6. A process in accordance with claim 2 wherein the alcoholate is sodium methoxide.

7. A process in accordance with claim 2 wherein the alcoholate is lithium methoxide.

8. A process in accordance with claim 2 wherein the alcoholate is sodium ethoxide.

9. A process in accordance with claim 2 wherein the alcoholate is potassium phenoxide.

10. A process in accordance with claim 2 wherein the alcoholate is tetramethylammonium methoxide.

11. A process in accordance with claim 2 wherein the alcoholate is a complex of 18-crown-6 ether and sodium ethoxide.

12. A process in accordance with claim 2 wherein the liquid phase includes an aprotic solvent medium.

* * * * *